United States Patent [19]

Patterson et al.

[11] Patent Number: 4,915,936

[45] Date of Patent: Apr. 10, 1990

[54] DENTAL HYGIENE COMPOSITION FOR REDUCING PERIODONTAL DISEASE

[75] Inventors: Lloyd D. Patterson, Ormond Beach; Jay W. Palmer, Tampa, both of Fla.

[73] Assignee: United States Gypsum Company, Chicago, Ill.

[21] Appl. No.: 264,526

[22] Filed: Oct. 31, 1988

[51] Int. Cl.$^4$ .......................... A61K 7/16; A61K 33/06
[52] U.S. Cl. ...................................... 424/49; 514/901; 424/696
[58] Field of Search .................... 424/49, 696; 514/901

[56] References Cited

U.S. PATENT DOCUMENTS

| | | | |
|---|---|---|---|
| 1,492,715 | 5/1924 | Kuerer | 424/49 |
| 1,817,664 | 8/1931 | Badanes | 424/49 |
| 3,574,824 | 4/1971 | Echeandia et al. | 424/50 |
| 4,097,604 | 6/1978 | Thiele | 424/318 |
| 4,214,006 | 7/1980 | Thiele | 424/318 |
| 4,224,307 | 9/1980 | Thiele | 424/49 |
| 4,447,254 | 5/1984 | Hughes et al. | 71/67 |
| 4,550,018 | 10/1985 | Ambike et al. | 424/52 |
| 4,687,663 | 8/1987 | Schaeffer | 424/52 |

FOREIGN PATENT DOCUMENTS

| | | | |
|---|---|---|---|
| 202359 | 11/1986 | European Pat. Off. | 424/53 |
| 269966 | 6/1988 | European Pat. Off. | 424/49 |
| 2922671 | 12/1980 | Fed. Rep. of Germany | 424/49 |
| 2510400 | 2/1983 | France | 424/49 |

OTHER PUBLICATIONS

David Horowitz, "Can A Toothpast Remove Placque?" 1985

*Primary Examiner*—Shep K. Rose
*Attorney, Agent, or Firm*—Robert H. Robinson; John M. Lorenzen; Robert M. Didrick

[57] ABSTRACT

Gingivitis and related periodontal problems of the gingival tissues may be treated with a dental hygiene composition comprising an effective amount of a calcium sulfate compound such as calcium sulfate hemihydrate. Preferred compositions comprise mouthwashes and oral rinses containing about 5–90% by weight of calcium sulfate hemihydrate, a liquid carrier such as water, a humectant and an alcohol.

8 Claims, No Drawings

DENTAL HYGIENE COMPOSITION FOR REDUCING PERIODONTAL DISEASE

BACKGROUND OF THE INVENTION

1. Field of the Invention

This invention relates to a dental hygiene composition for treating gingivitis and related periodontal diseases. More particularly, it relates to a dental hygiene composition for treating periodontal diseases based upon a calcium sulfate compound.

2. Description of the Prior Art

Certain calcium phosphate salts, such as dicalcium orthophosphate dihydrate, have been used in oral preparations such as toothpastes for the polishing and abrasive effects which they provide. Hydroxylapatite, another calcium phosphate salts, has been used in a gel formulation to promote remineralization of tooth enamel, as set forth in U.S. Pat. No. 3,679,360. Synthetic fluoroapatite has also been suggested for use in dental preparations to prevent dental caries, as set forth in U.S. Pat. No. 4,139,599.

The search for new dental compositions having therapeutic value continues, particularly products for the treatment of epitheleum and gingival tissue to heal periodontal aggravation. Periodontal disease often is caused by excessive tartar deposits and chronic dental plaque build-up. Advanced periodontal disease is the primary cause of tooth loss in persons over 40 years of age, whereas a mild periodontal disease, gingivitis, frequently occurs in young people under 18 years of age. There are several methods used for treatment of periodontal disease under professional dental supervision, but generally there have been no effective methods available to the individual to treat these problems without professional dental care, beyond good oral hygiene (brushing and flossing).

Plaque is a growth of normal mouth micro-organisms on tooth surfaces. Apparently, plaque does not become sufficiently toxic to initiate gingival inflammation in less than about three days. The bacteria attach to the saliva on teeth and tissues where they convert simple sugars carried in the saliva into sticky carbohydrates which accumulate and become plaque. Unless removed effectively within that time, plaque can build up and form a hardened deposit of tartar that can cause irritation of the gums, which may lead to gingivitis and other serious gum diseases. Thus, there is a need for dental compositions which allow the individual to treat periodontal problems apart from professional dental supervision and care.

U.S. Pat. Nos. 4,097,604; 4,214,006; 4,224,307 and also 4,550,018 propose treating gingivitis with certain fatty acids or their salts. Further, it is known to use a calcinated sodium sulfate in the preparation of a flavored composition which may be used as an addition to mouthwash, as disclosed in U.S. Pat. No. 1,580,952. In addition, it is known to use calcium sulfate hemihydrate, calcined gypsum or plaster of Paris, for the controlled release of trace elements into drinking water as disclosed in U.S. Pat. No. 4,447,254.

SUMMARY OF THE INVENTION

It has now been found that gingivitis and related periodontal diseases of the gingival tissues may be effectively treated with a calcium sulfate compound. A liquified calcium sulfate composition has been found to be effective for treating periodontal diseases and related problems. The calcium sulfate compositions reduce gingival inflammation, periodontal pockets, and may stabilize the attachment of loose teeth. Further, treatment with the calcium sulfate compositions appears to inhibit calculus and plaque formation in the presence of salivary fluids.

This invention relates to a dental composition for oral rinse or mouthwash applications which comprises a carrier and from about 5% to about 90% by weight of a calcium sulfate compound. Preferably, the composition is liquified and contains an effective amount of glycerin or similar humectant to aid the deposition and adherence of the calcium sulfate to the teeth and tissues. In addition, it is preferred that the liquified composition contain an effective amount of a set inhibiting agent for the calcium sulfate, such as ethanol, when the calcium sulfate is present in a hydratable or settable form such as the hemihydrate.

It is an object of this invention to provide a dental hygiene composition and a method for treating gingivitis and related periodontal diseases of the gingival tissue based upon contacting the gingival tissue with the composition comprising a calcium sulfate compound.

Other objects of the present invention will become apparent as the compositions and method for treating periodontal diseases is described hereinafter.

DETAILED DESCRIPTION OF THE PREFERRED EMBODIMENTS

In one preferred embodiment, an oral rinse composition is prepared comprising a substantial amount of calcium sulfate hemihydrate, such as about 10–80% by weight of the total composition; a liquid carrier such as distilled water; an effective amount of a set inhibiting agent for the calcium sulfate hemihydrate, such as about 20% ethanol; and an effective amount of a humectant to aid adherence of the calcium sulfate to teeth and tissue, such as about 8% glycerin. The pH of the liquified composition is between about 5 and 7. Typically, the pH of salivary fluids in the human mouth varies between about 4.5 and 7.5. This formulation is preferred for use as an oral rinse or mouthwash.

The oral rinse composition should be shaken well before usage. As an example of a treatment for gingivitis, one-half fluid ounce twice a day may be used as a rinse, being kept in the mouth for five minutes and allowed to flow around all of the teeth-gingival line area. The formulation may also be utilized with a toothbrush involving normal brushing technique, cleansing the teeth down to the gum. In both cases, patients are advised not to rinse the mouth with water for at least 10 minutes following treatment.

The essential active ingredient in the above oral rinse formulation is any C.P. grade of calcium sulfate hemihydrate ($CaSO_4 \cdot \frac{1}{2}H_2O$). The calcium sulfate compound may be from any natural source such as gypsum rock, preferably calcined to the beta hemihydrate form and meeting FDA and Codex requirements as to purity. Calcium sulfate synthesized from various chemical processes may be used, such as the by-product chemical gypsum from citric acid manufacture, with appropriate calcination of dihydrate forms or hydration of anhydrite forms to the preferred hemihydrate form. Though calcium sulfate hemihydrate is preferred, other calcium sulfate compounds such as the dihydrate and the soluble anhydrite, may be used.

The calcium sulfate compound is desirably incorporated into dental products such as tooth gels, emulsions, suspensions, solutions, mouthwashes and pastes for topical application to the teeth and gum line in an amount ranging from about 5% to about 90% by weight of the dental composition. Preferably, about 10-80% by weight of the dental composition is a calcium sulfate compound, and this generally provides for effective treatment of gingival related diseases by oral administration. As a dental rinse or mouthwash, calcium sulfate concentrations of about 10-50% by weight appear to give best performance. For use as a concentrated gel, it is currently preferred that the amounts of calcium sulfate range between about 10-80% by weight.

Certain types of liquid dental hygiene formulations, especially mouthwashes and rinses, conventionally contain substantial quantities of ethanol as an astringent and antiseptic agent. It has been found that the presence of a minor amount of alcohol extends the shelf life of formulations containing the desired calcium sulfate hemihydrate. Ethanol or higher alcohols such as propanols and polyethylene glycols inhibit rehydration of calcium sulfate hemihydrate suspended in aqueous carriers. The dental compositions in accordance with the invention that are formulated as liquid mouthwashes or rinses containing relatively large quantities of water, e.g. in the range of about 40 to 90% by weight, should contain at least about 5% and preferably 8-25% by weight of an alcohol such as ethanol to extend the shelf life of the hemihydrate form. The amount of such alcohol may be reduced to about 1-5% or less depending upon the amount of water present, the desired degree of astringency, and the importance of shelf life. Of course, other known astringent and/or antiseptic agents may be utilized in customary amounts in place of or as supplements to the preferred ethanol.

The dental hygiene composition may also contain the conventional humectants such as glycerin and/or sorbitol. It has been found that glycerin acts as an excellent liquid viscosity control agent which aids flow into periodontal areas and improves adhesion to tissue. The polyhydric alcohol seems further to facilitate removal of soft plaque and stain from the teeth. It is believed that similar polymeric glycol humectants which provide more of a thickening action, would also provide this increased adhesion and assist in removing sticky carbohydrates and soft plaque from teeth when treated with the calcium sulfate of the invention. Examples of these are carboxymethyl cellulose derivatives and/or polyethylene glycols, polypropylene glycols and the like. They may be used alone or in combination. In the case of compositions of low solids content with relatively large quantities of water, such as in the case of mouthwashes or rinses, the humectant may be present in amounts of up to about 20% by weight, more typically around 5-10%. In the case of toothpastes, gels and products where the liquid content plays a more important role in providing a desired consistency and viscosity, somewhat greater quantities of humectant, e.g. in the range of 20 to 40% by weight, may be used.

Typically, liquid dental hygiene formulations conventionally contain a physiologically acceptable pigment, sweetener, e.g. sucrose, sodium saccharin or sodium cyclamate or the like, and an essential oil flavor and other additives. The compositions of the invention may be so augmented, e.g. as by flavoring with thymol, eucalyptol methyl salicylate, or peppermint and spearmint oils, in customary amounts, typically about 0.2-3.0% by weight in the case of compositions containing water or an aqueous vehicle carrier. These oils may, if necessary, be maintained in dispersion with the aid of suitable dispersing agents, generally in an amount of from 0.1 to 0.2% or more. Typically, especially in the case of toothpaste and powder formulations, the dentrifice may contain about 10-50% by weight of a particulate dental abrasive as well as whiteners, brighteners and other additives. Materials which enhance fluoroapatite formation may be included.

EXAMPLE 1

The effect of an oral rinse on stained salivary pellicle accumulation and on softening calculus were studied in vitro.

In one study, a dozen extracted human teeth with abundant accumulations of calculus were mounted in acrylic blocks for each test material. The teeth were weighed, immersed in either deionized water or an oral rinse for 60 minutes, brushed on a V-8 cross brushing machine for 1000 strokes using an Oral B-40 toothbrush at 150 gram tension and a slurry of silica based toothpaste, and reweighed for calculus removal.

The oral rinse comprised about 16% calcium sulfate hemihydrate, about 21% ethanol, about 8% glycerine and about 55% by weight distilled water.

The mean reduction in specimen weight was 9.25 mg with the deionized water and 10.80 mg with the oral rinse. This weight reduction with the oral rinse may indicate a trend toward calculus softening, and if used with brushing to attack calculus deposits before they become calcified may provide a substantially greater benefit.

EXAMPLE 2

In another study, sixteen bovine permanent central incisors per test material were cut to obtain labial enamel specimens of approximately 10 square millimeters. The specimens were embedded in an autopolymerizing methacrylate resin so that only the enamel surfaces were exposed, lightly etched and then pretesting reflectance values were determined. Thereafter, the specimens were placed on a rotating rod and immersed in test solutions. The various test regimens were as follows:

Group 1: Immerse in saliva for 1 hour, immerse in coffee/tea/ferric chloride solution for 30 minutes and immerse in deionized water for 1 minute.

Group 2: Same as Group 1 except oral rinse substituted for deionized water.

Group 3: Same as Group 1 except saliva was mixed with deionized water in 10:1 proportions.

Group 4: Same as Group 3 except saliva was mixed with oral rinse 10:1 proportions.

Thus, Groups 1 and 2 evaluated the oral rinse as an enamel surface treatment while Groups 3 and 4 evaluated the oral rinse as a chemical inhibitor in association with the salivary component of the pellicle. The oral rinse had the same formulation as in Example 1.

The sequential treatment regimen was continued through 47 cycles and reflectance values determined to establish the amount of pellicle staining.

The results of this study are summarized as follows (note: a higher light reflectance number is indicative of less staining):

| Treatment | Mean Stained Pellicle Reflectance Scores | | |
|---|---|---|---|
|  | Pre-Test | Post-test | Difference |
| Group 1-water | 64.0 | 24.7 | 39.3 |
| Group 2-oral rinse | 63.8 | 23.8 | 40.0 |
| Group 3-water in saliva | 63.9 | 25.9 | 38.0 |
| Group 4-oral rinse in saliva | 63.9 | 29.5 | 34.0 |

Comparing Groups 3 and 4 of this test, when the oral rinse was used as a chemical inhibitor in association with the salivary fluid protein source for the pellicle (Group 4), there was a significant reduction in stain accumulation.

EXAMPLE 3

Controlled clinical evaluations were performed with dental patients utilizing a preferred formulation comprising about 16% calcium sulfate hemihydrate, about 21% ethanol, about 8% glycerin and about 55% distilled water (all percentages by weight), with a small amount of vanilla extract being added as desired for certain of the patients. Patients selected for treatment involved a variety of periodontal problems: some of them had experienced periodontal disease to varying degrees for years with extensive treatment having been provided, including gingivectomy and gingivalcureatage, although experiencing continuing problems. Others selected, in an age span of patients ranging from young adults to senior citizens, included persons who had not used professional dental services in some time and did not provide themselves with good oral hygiene techniques. Each patient was examined, full mouth X-rays were taken to verify problems before treatment, and if periodontal pockets existed, measurements were taken and charted with an 18 millimeter pocket gauge. The patients were provided with samples of the oral rinse and instructed to follow one or both of the following procedures:
(1) Shake the bottle well before using; use one-half fluid ounce twice a day as a mouth rinse, holding the formulation in the mouth cavity for five minutes and allowing it to flow around all teeth, and do not rinse mouth with water for at least 10 minutes following usage.
(2) Rinse and brush: shake the container well before using; use one-half fluid ounce twice a day. On the first day only, use the formulation as a rinse allowing it to flow around all teeth while keeping it in the mouth cavity for five minutes. Thereafter, continue treatment by using the formulation with a toothbrush and normal brushing technique, cleansing the teeth down to the gingival gum. Do not rinse with water for at least 10 minutes Exemplary results from a small clinical study of patients were as follows:

Case 1—The patient was a male in his late twenties experiencing serious gingivitis condition with heavy dental plaque and tartar deposits. All gingival tissue was very inflamed with considerable anterior gingival "bleeding". Following one week of rinse procedure #1, gingival bleeding had stopped and tissue in general appeared improved.

Case 2—The patient was a male in his late fifties being treated for periodontal problems for the past 10 years, including three series of gingivectomy procedures. X-ray examination indicated some bone absorption in both upper and lower posterior regions. The posterior teeth were sensitive, with lingual gingival tissue loss evident on the upper right second molar. Following two weeks of rinse procedure #1, sensitivity of teeth improved. Within five weeks of treatment, tissue on the lingual surface of the upper molar appeared improved, with less recession. At the end of the fifth week, all gingival tissue appeared very firm with no inflammation.

Case 3—The patient was a fifty year old male with a mild gingivitis and upper anterior tissue reduction periodontal problem. Patient had received professional periodontal treatment six months prior which improved the situation but continued to have periodontal problems. Using rinse and brush procedure #2, gingivitis condition was eliminated within a four week period. Patient commented upon improved condition in the "brightness" of the teeth and a "clean" feeling.

Case 4—The patient was a sixty year old female exhibiting gingivitis with serious receding of the gums, some loosened lower anterior teeth, 5-6 millimeter pockets on the left second upper molar and right second lower molar. Considerable sensitivity of all teeth was evident. Patient had all tartar removed professionally two months prior to starting rinse treatment, and left lower central removed because of bone absorption. X-ray examination showed bone absorption prevalent throughout both ridges.

Treatment was started with rinse procedure #1. At the completion of one week, the gingivitis problem had receded, and the gum tissue became much more firm and less inflamed. Within four weeks of treatment, gingivitis had completely been eliminated and the pockets on both upper and lower molars had been reduced considerably. Comments from the patient indicated that prior sensitivity had disappeared. Within eight weeks, the lower anterior had become rigid.

Following eight weeks of treatment, the patient was advised to stop the rinse treatment for four weeks. The purpose of this was to see if initial problems would re-occur. Examination showed no change in tissue during the first three weeks without treatment but inflammation of tissue showed in the fourth week. The rinse and brush procedure #2 was started and tissue inflammation ceased. Within four weeks on procedure #2, patient had no tissue inflammation, all teeth were very rigid, and pockets were reduced almost 100% from initial starting of treatment 16 weeks earlier.

Having described the dental hygiene compositions of this invention, what is claimed is:

1. A dental hygiene composition comprising water and which contains about 16% by weight of calcium sulfate hemihydrate, about 21% by weight ethanol and about 8% by weight glycerin.

2. A dental hygiene composition in the form of a mouthwash comprising from about 40 to about 90% by weight of water, about 5% to about 50% by weight of a calcium sulfate compound, from about 1% to about 25% by weight of an alcohol and from about 5% to about 20% by weight of a humectant.

3. The composition of claim 2 in which the calcium sulfate compound is calcium sulfate hemihydrate in an amount from about 10 to about 50% by weight.

4. The composition of claim 3 which contains at least about 5% by weight of an alcohol.

5. The composition of claim 4 which contains glycerin as a humectant.

6. The composition of claim 2 which contains from about 8% to about 25% ethanol.

7. The composition of claim 2 in which the humectant is glycerin in an amount from about 5 to about 10% by weight.

8. The composition of claim 7 which contains about 15% by weight calcium sulfate hemihydrate, about 20% by weight ethanol, about 8% by weight glycerin and the balance is water.

* * * * *